United States Patent [19]

Janin et al.

[11] 4,266,874

[45] May 12, 1981

[54] APPARATUS AND METHOD FOR MEASURING THE SIZE OF FIBERS

[75] Inventors: Gerard Janin, Essey les Nancy; Jean-Marie Ory, Heillecourt, both of France

[73] Assignee: Institut National de la Recherche Agronomique, Paris, France

[21] Appl. No.: 957,679

[22] Filed: Nov. 6, 1978

[30] Foreign Application Priority Data

Nov. 7, 1977 [FR] France .................. 77 33441

[51] Int. Cl.³ .................. G01N 15/02; G01N 21/23; G01N 21/05
[52] U.S. Cl. .................. 356/335; 356/365; 356/440
[58] Field of Search .................. 356/335–343, 356/365, 440–442; 250/222 PC; 374/71 CP; 73/DIG. 8, 53, 63

[56] References Cited

U.S. PATENT DOCUMENTS

| Re. 29,141 | 2/1977 | Hogg | 356/335 |
|---|---|---|---|
| 3,548,206 | 12/1970 | Ogle et al. | 324/71 CP |
| 3,689,833 | 9/1972 | Hogg | 324/71 CP |
| 3,705,348 | 12/1972 | Jacobs | 324/71 CP |
| 3,787,123 | 1/1974 | Sigrist | 356/338 |
| 3,831,028 | 8/1974 | Kerlman et al. | 356/365 |
| 3,856,408 | 12/1974 | Hill et al. | 356/365 |
| 3,941,477 | 3/1976 | Schodl | 356/343 |
| 4,110,043 | 8/1978 | Eisert | 356/336 |

Primary Examiner—John K. Corbin
Assistant Examiner—Wm. H. Punter
Attorney, Agent, or Firm—Cushman, Darby & Cushman

[57] ABSTRACT

In an apparatus for measuring the sizes of fibers, said fibers are diluted into a carrier liquid in a container. The liquid is circulated by means of a pump in a main pipe through a chamber in which a vortex flow exists. A part of the liquid in the chamber is derivated through a small diameter pipe towards a photo-electric analyzing equipment.

9 Claims, 5 Drawing Figures

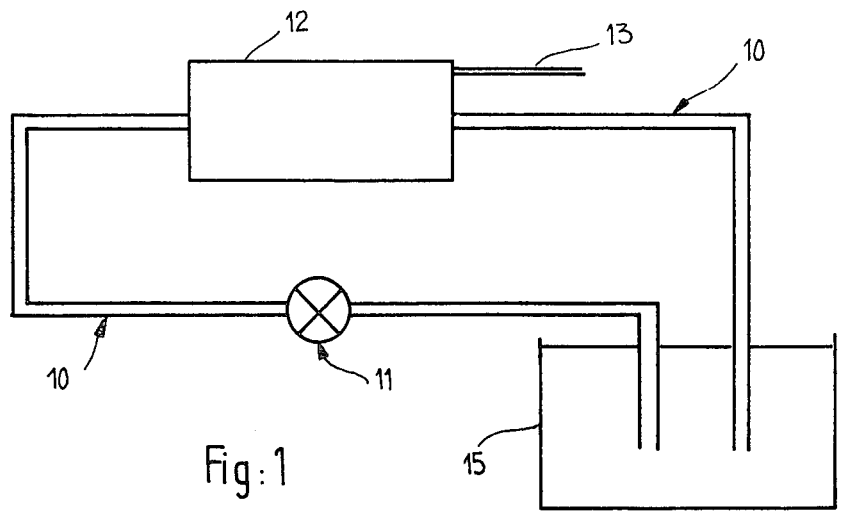
Fig. 1
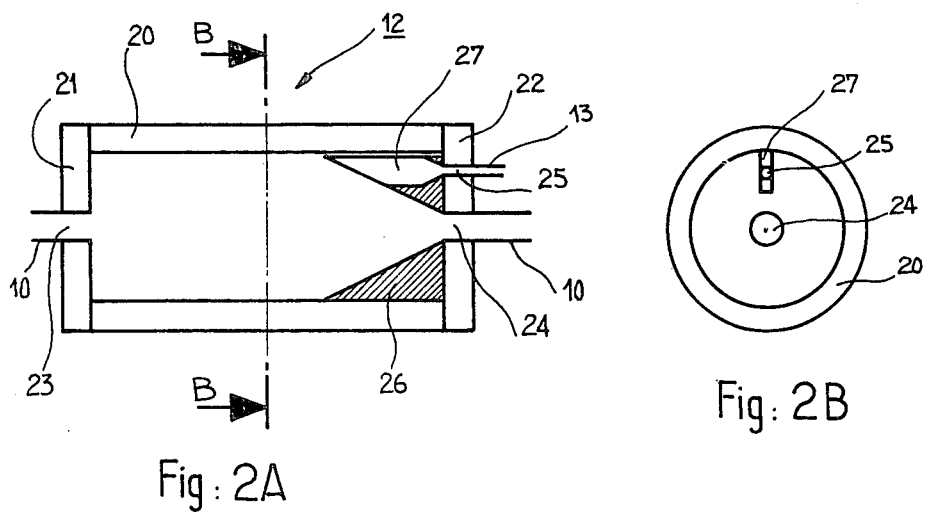
Fig. 2A
Fig. 2B
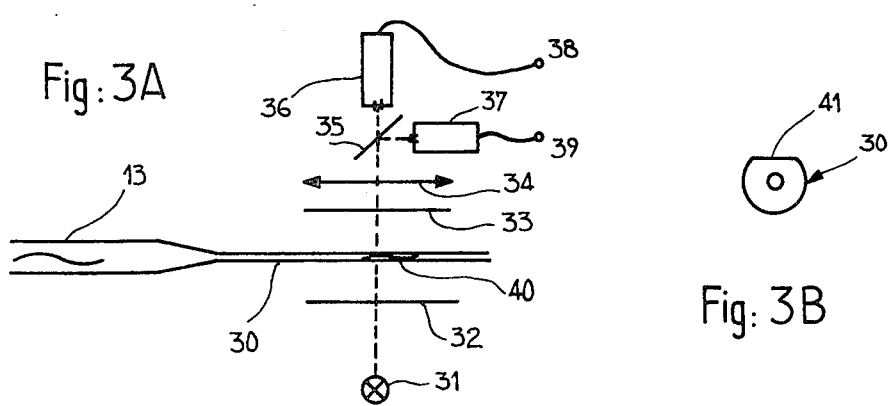
Fig. 3A
Fig. 3B

APPARATUS AND METHOD FOR MEASURING THE SIZE OF FIBERS

FIELD OF THE INVENTION

The invention relates to a method and a device for automatically measuring the size of fibers and in particular wood fibers.

Generally, for studying the qualities of a wood, one of the most important features lies in the study of the delignified fibers, either as regards woods for making a paper paste or timbers. Accordingly, the improvement of the species and the selection of the families or the study of the influence of the various environment factors on a wood implies studying the length of fibers, that is knowing precisely the average length of the fibers of a same batch and in particular the distribution of the lengths.

BACKGROUND OF THE INVENTION

In the prior art, for making this measurement, a manual operation was undertaken. An operator arranged the dried fibers between two glass plates and projected the image thereof on a large screen. The length of the fibers was measured on the projection screen, for example by means of measuring curvimeters used for reading maps or measuring wheels provided with an electronic device such as a photodiode lighted through a wheel provided with thin equidistant slots which accordingly permits to measure the path of the wheel and therefore the length of the fibers on the screen by counting the pulses which are recorded by a data sensor. Those prior art devices are known under the name of semi-automatic sensors. This operation is particularly long and tedious and therefore, in spite of the semi-automatic recording electronic device, only a small number in the range of 50 fibers of a sample was usually measured. Additionally, even in a not conscious way, the operator has a tendency to make a choice or a selection among the measured fibers. In particular, he has a tendency to measure the longest or the nicest elements whereby the consequent statistics are erroneous.

One can easily imagine the time which will be necessary for making a measure on samples corresponding to 50 twenty-year old trees for, for example, a fertilization test with 7 treatments would require $50 \times 20 \times 7 \times 50 = 350,000$ fibers to be measured. Additionally, the effects of the age of the trees, of the orientation in the forest and of the height of the sample, result in a very great number of samples. Accordingly, the operator is tempted to limit the number of measured fibers for each sample and unfortunately chooses very often a number smaller than 50, such a number being not sufficient for permitting the obtention of good statistical measures.

OBJECTS OF THE INVENTION

Accordingly, a main object of the instant invention is to render automatic all the operation of measurement of the fiber length for eliminating the discrimination made by an operator, decreasing the elementary time duration of the measurement, and allowing to increase in an important way the number of measurements made on one sample.

An apparatus for measuring the size of the wood fibers according to the invention comprises a main closed circuit for circulating a liquid wherein is diluted a fiber sample; a derivation circuit towards a pipe having a small diameter with respect to the length of the fibers, wherein is drawn a small part of the liquid of the main circuit; and means for measuring the size of the fibers while they are passing through the derivation circuit wherein a laminar flow exists.

In the derivation circuit there is provided a transparent tube having a small diameter arranged between crossed polarizers and lighted by a light source. Accordingly, through the analyzer, due to the birefringency of the wood fibers, an observator can see only the lighted fibers on a black background. The image of the fibers is sent to photoreceiving means which provide pulses corresponding to the passing of the fibers. The time duration of the pulses corresponds to the length of the fibers, the height of the pulses to their diameter and the surface of the pulses to the longitudinal section surface of the fibers.

BRIEF DESCRIPTION OF THE DRAWINGS

Those objects, characteristics and advantages and others of the invention will be explained in detail in the following description of preferred embodiments made in connection with the attached drawings wherein:

FIG. 1 generally shows a device comprising a closed circuit and a derivation circuit according to the invention;

FIGS. 2A and 2B are longitudinal and transversal croos-sections of a chamber of the circuit of FIG. 1;

FIG. 3A schematically shows an optical analyzing device according to the invention; and FIG. 3B is a cross-section view of the capillary tube shown in FIG. 3A.

DETAILED DESCRIPTION OF THE INVENTION

FIG. 1 schematically shows a device for randomly selecting fibers according to the invention. A liquid circulates in a pipe or conduit 10 under the action of a pump 11, this liquid being for example contained in a container 15. In the circuit of the pipe 10 is provided a chamber 12 comprising a derivation output 13 in which the liquid is pushed due to the effect of the pump 11. The internal structure of the chamber 12 is chosen as a function of the liquid speed in order to obtain a vortex flow. Accordingly, a random portion of the liquid contained at each instant within the chamber 12 flows through the derivation pipe 13. This pipe 13 is connected to an analysing circuit which will be disclosed hereafter and which comprises at least a part having a section much smaller than the section of the pipe 10. The container 15 is filled with a liquid, for example water, to which is added a small quantity of a liquid containing delignified wood fibers to be studied, a suitable stirring being provided for insuring a good mixture of the fibers. So, according to an aspect of the invention, it is not necessary to dry the delignified wood fibers and to arrange same on a plate.

FIGS. 2A and 2B show respectively a longitudinal and a transversal cross-section according to the line B—B of a preferred embodiment of the chamber 12 permitting to obtain a vortex flow necessary to the random derivation of the fibers into the pipe 13. The chamber 12 comprises a cylindrical wall 20 closed by two plates 21 and 22. The plate 21 comprises an opening 23 for insuring the connection with one of the open ends of the conduit or inlet pipe 10 and the plate 22 comprises a first opening 24 for connection with another of the main open ends of the conduit or outlet pipe 10 and an opening 25 for connection with the derivation pipe 13. Inside the cylinder 20, and close to the plate 22, is arranged a torus having a triangular section 26 as shown in FIG. 2A. The opening 24 corresponds accordingly to the end of a funnel. From the wall of the torus 26 is formed, for example by means of a saw, a slot 27 connected with the opening 25. Accordingly, the fibers are whirling at the inside of the funnel formed by the tore 26 and some of them are randomly derivated through the slot 27 and progressively directed towards the derivation 13.

FIG. 3A schematically shows the optical equipment for detecting the fibers circulating in the derivation 13 according to the invention. The derivation 13 is connected with a tube 30 having a small diameter with respect to the fiber length and which will be called hereafter the capillary. The diameter of this capillary 30 can, for example, be of about 0.2 mm. In fact, for indicating a size range, the length of the fibers for a resinous wood is substantially comprised between 1.5 and 8 mm, the average value being substantially between 3 and 4 mm. For leafy woods or hard woods, this fiber length is substantially comprised between 0.25 mm and 2.5 mm, the average being substantially of about 1.5 mm.

According to an axis perpendicular to the axis of the capillary 30 is arranged an optical system comprising a light source 31, a polarizer 32, an analyzer 33, a lens 34, a semi-transparent plate 35 and a photomultiplier or other electro-optic transducer 36. The semi-transparent plate 35 reflects also a part of the beam emitted by the light source 31 towards a second photomultiplier 37. The photomultipliers 36 and 37 have output terminals 38 and 39 respectively. The lens 34 operates for forming the image of a fiber 40 moving into the capillary 30 on the image plane of the forward face of the photomultiplier 36 comprising the input slit thereof. This image plane corresponds, due to the presence of the semi-transparent plate 35, to the forward face of the photomultiplier 35. It will be noted that the set comprising the lens 34 and the semi-transparent plate 35 can be replaced by a binocular telescope.

The capillary tube 30 is arranged between the polarizers 32 and 33 as the wood fibers are practically not visible in the liquid in which they are immersed and do not permit to obtain a signal at the photomultipliers by a direct occultation of the light beam. However, the wood fibers present some birefringence. So, the polarizer 32 and the analyzer 33 being crossed, in the absence of fibers in the field of the lens 34, a black background appears and it is only when a fiber arrives in the field of the lens 34 that its image is projected under the form of a light strip in the image plane of said lens. It has been assumed in the above that the liquid in which are immersed the fibers was itself presenting no birefringence and no rotary power. This liquid will be preferentially pure water.

In the determination of the image plane of the lens 34, the lens effect due to the capillary 30 has to be taken into account, said capillary having for example a cross-section as shown in FIG. 3B and comprising a flattened surface 41 on the upper side, towards the lens 34.

Accordingly, at the output 38 of the photomultiplier 36 provided with an input slit, a pulse is obtained in correspondance with each pass of wood fiber 40. The time duration of the pulse if proportional to the length of the fiber and the magnitude of the pulse is proportional to the diameter of the fiber. In other words, the surface of the pulse is proportional to the longitudinal cross-section of the fiber. The apparatus according to the invention permits accordingly not only the measurement of the length of the fibers, but also of the average diameters of the fibers, which constitutes an important parameter for a great number of practical applications.

Of course, if the length of the pulse at the output 38 is proportional to the length of the fiber, it is also proportional to the speed of the fiber. Said speed can be determined by mechanical means. It is preferentially and more precisely determined by using the second photomultiplier 37 by off-setting slightly the input slit thereof on the image plane with respect to the input slit of the first photomultiplier 36. For example, if the distance between those two input slits considered on the same image plane corresponds to a distance of, for example, 1 mm at the level of the capillary, the time spent between the positive-going flanges of the pulses at the terminal 38 and the terminal 39 represents the time spent by the fiber to move of 1 mm, that is the speed of the fiber.

The various electronic circuits useful for displaying length and section information of the fibers will not be disclosed in detail as they are well known in the art and can be ordered to any person skilled in the art of electronics to whom the available inputs and the outputs to be displayed have been indicated. It will be also noted that, due to the presence of the information in an electric form, it is simply possible, by means of microprocessors suitably programmed or wired, to make direct calculations on the average length of the fibers and the standard deviation. Again, the obtention of those results by electronic means can be made by any person skilled in the art of electronics.

As a numerical example, it will be noted that, in a practical experiment, we have carried out a device according to the invention by providing a capillary 30 having a diameter of 0.2 mm and a main circuit 10 having a diameter of 10 mm, the chamber 12 having a diameter of substantially 100 mm. One has obtained a random selection of the fibers towards the derivation and a laminar flow of the liquid in this derivation at the capillary.

It will be noted that the various shapes and structures shown in particular in FIGS. 2A, 2B, 3A and 3B constitute elements of the invention.

Of course, the invention can be applied to other fibers than wood fibers.

What we claim is:

1. An apparatus for measuring the size of fibers, comprising:
   a main circuit wherein a main flow of a liquid having a fiber sample diluted therein is caused to circulate;
   a derivation circuit having a portion of small diameter with respect to the length of the fibers to be measured providing a laminar flow;
   said main circuit including a chamber, said derivation circuit extending from said chamber, said chamber including means for creating therein a vortex flow so as to divert randomly a portion of the fibers circulating in said main circuit into said derivation circuit, in a secondary flow; and
   optical means for measuring the size of the fibers as they pass in said portion of small diameter of said derivation circuit;
   wherein said main circuit includes:
   a conduit having open first and second ends terminating at opposite ends of said chamber, said chamber having a substantially elongated cylindrically shaped portion having a longitudinal axis, said chamber having longitudinally opposed inlet and outlet walls respectively connected to said first and second conduit ends, said chamber cylindrically shaped portion having a cross-sectional area greater than the cross-sectional areas of said conduit ends, said conduit ends being substantially aligned with said axis, said chamber having an outlet end portion with an inner wall coverging downstream for connection to said second conduit end of said main circuit, said derivation circuit having an inlet opening into said inner wall of said outlet end portion of said chamber.

2. An apparatus according to claim 1, wherein said inlet opening of said derivation circuit has the shape of a radial slot formed in said inner wall of said outlet end portion of said chamber.

3. An apparatus according to claim 2, wherein said portion of small diameter of said derivation circuit includes a transparent tube and wherein said optical means for measuring the size of the fibers comprise means for imaging the fibers and photoelectric and electronic means for detecting the images of the fibers and for providing values of the length and diameter of the fibers circulating in said derivation circuit.

4. An apparatus according to claim 3 wherein said measuring means further comprise means for measuring the velocity of the fibers.

5. An apparatus according to claim 3 wherein the optical means comprise polarization means adjusted for obtaining the extinction of an analysis light beam in the absence of fiber in said transparent tube.

6. A method for measuring the size of fibers, which comprises the following steps:
diluting a fiber sample in a carrier liquid;
circulating the liquid carrying the fibers in a main circuit;
randomly diverting a part of the circulating liquid and directing same toward a transparent tube having a small diameter with respect to the average length of the fibers;
imaging the diverted fibers during their pass through said transparent tube at an image plane;
arranging a slit photodetector in said image plane for obtaining pulses during the pass of the diverted fibers;
measuring the time duration of the pulses;
measuring the amplitude of the pulses;
imaging the diverted fibers during their pass through said transparent tube at a second image plane;
arranging a second slit photodetector at the second image plane;
shifting the slit of the second photodetector with respect to the one of the first photodetector by a determined quantity;
measuring the time interval between the positive edges of the pulses provided by the first and second photodetectors;
utilizing this interval information for determining the velocity of the fibers circulating in said transparent tube; and
combining this velocity information with the pulse duration information for determining the length of the diverted fibers.

7. A method as in claim 6 wherein said step of randomly diverting includes the steps of:
creating a vortex flow of said circulating liquid; and
diverting a part of said vortex flow toward said transparent tube.

8. A method according to claim 6, wherein the steps of image formation of the fibers comprise the steps of providing polarization means for obtaining an extinction of the analysis beam in the absence of fibers in the transparent tube.

9. An apparatus for measuring the size of fibers, comprising:
a main circuit wherein a main flow of a liquid having a fiber sample diluted therein is caused to circulate;
a derivation circuit having a portion of small diameter with respect to the length of the fibers to be measured providing a laminar flow;
said main circuit including a chamber, said derivation circuit extending from said chamber, said chamber including means for creating therein a vortex flow so as to divert randomly a portion of the fibers circulating in said main circuit into said derivation circuit, in a secondary flow; and
optical means for measuring the size of the fibers as they pass in said portion of small diameter of said derivation circuit;
wherein said main circuit includes:
a conduit having open first and second ends terminating at opposite ends of said chamber,
said chamber having walls defining the boundaries of an elongated open space including a first elongated cylindrically shaped space disposed adjacent said first conduit end having a longitudinal axis and a cross-sectional area in a plane perpendicular to said axis greater than the cross-sectional areas of said conduit first and second ends, and a second space converging downstream to said second conduit and said conduit ends being substantially aligned with said axis,
said derivation circuit having an inlet opening into the portion of said walls defining the boundaries of said second space.

* * * * *